Figure 1:
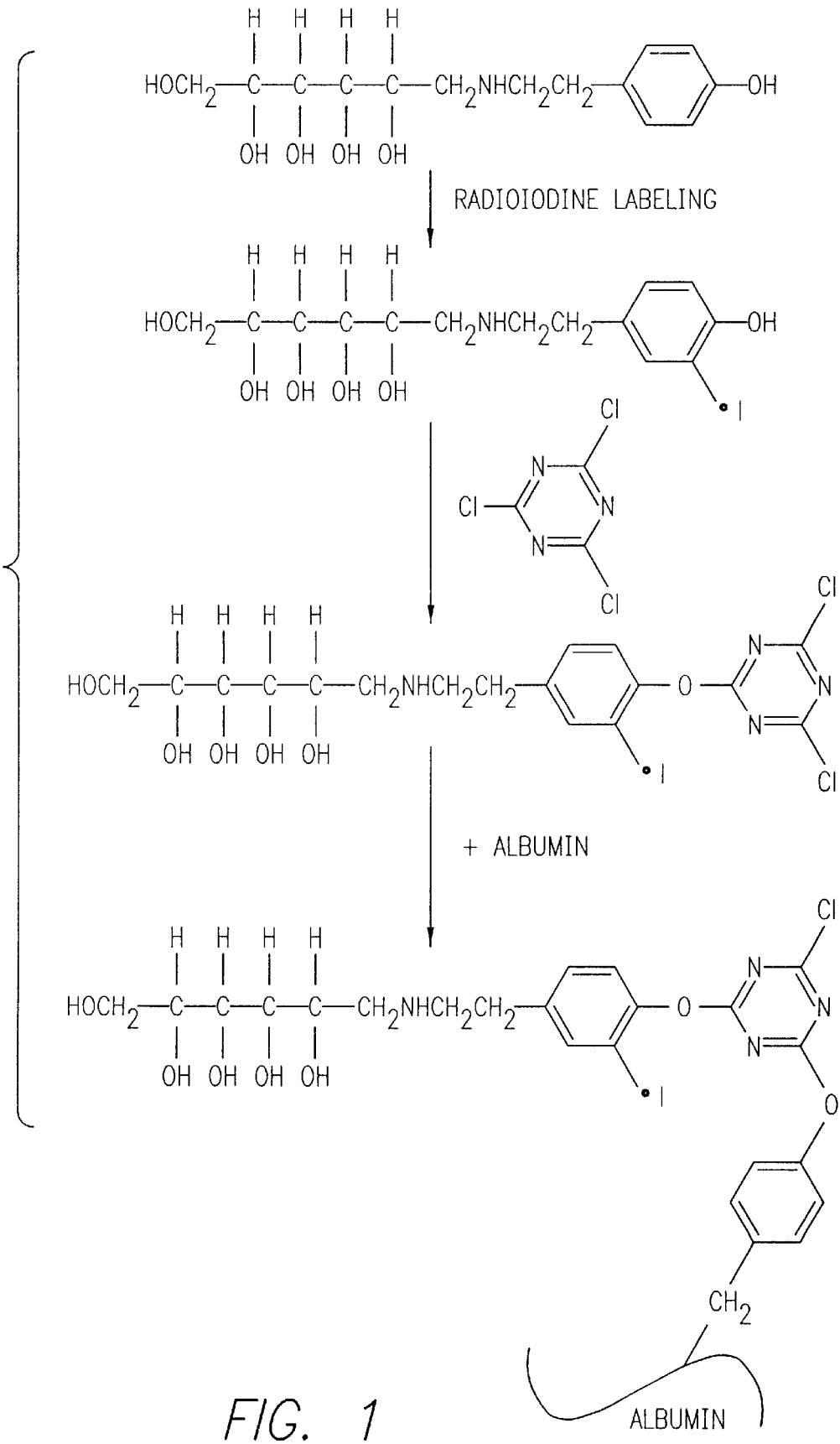

United States Patent [19]
Sinn et al.

[11] Patent Number: 5,906,977
[45] Date of Patent: May 25, 1999

[54] CONJUGATE FOR TREATING INFLAMMATORY DISEASES

[75] Inventors: Hansjörg Sinn, Wiesloch; Hans-Hermann Schrenk, Zeiskam; Wolfgang Maier-Borst, Dossenheim; Gerd Stehle, Mannheim; Andreas Wunder, Eppelheim; Dirk Hoff-Biederbeck, Ludwigshafen; Dieter Ludwig Heene, Mannheim, all of Germany

[73] Assignee: Deutsches Krebsforschungszentrum Stiftung des offentlichen Rechts, Heidelberg, Germany

[21] Appl. No.: 08/817,678

[22] PCT Filed: Sep. 26, 1995

[86] PCT No.: PCT/DE95/01337

§ 371 Date: Sep. 23, 1997

§ 102(e) Date: Sep. 23, 1997

[87] PCT Pub. No.: WO96/10422

PCT Pub. Date: Apr. 11, 1996

[30] Foreign Application Priority Data

Sep. 30, 1994 [DE] Germany .............................. 44 35 087

[51] Int. Cl.$^6$ .......................... A61K 38/38; A61K 38/40; A61K 31/65; A61K 31/33; A61K 31/50
[52] U.S. Cl. ........................... 514/12; 514/152; 514/183; 514/249
[58] Field of Search .............................. 514/12, 152, 183, 514/249

[56] References Cited

U.S. PATENT DOCUMENTS

| | | |
|---|---|---|
| 4,466,951 | 8/1984 | Pittman . |
| 5,308,604 | 5/1994 | Sinn et al. . |
| 5,382,657 | 1/1995 | Karasiewicz et al. . |
| 5,622,685 | 4/1997 | Sinn et al. . |

FOREIGN PATENT DOCUMENTS

| | | |
|---|---|---|
| 882 541 | 7/1980 | Belgium . |
| 0 398 024 | 11/1990 | European Pat. Off. . |
| 40 17 439 | 12/1991 | Germany . |
| WO 93/03035 | 2/1993 | WIPO . |

OTHER PUBLICATIONS

Bartilini et al, Derwent World Patent Index File, abstract No. 92–142656, 1992.

Hamblin et al., "Conjugates Between Proteins and Fluorescent Dyes as Potential Photosensitizers," *Photodynamic Therapy and Biomedical Lasers,* Proceedings of the International Conference on Photodynamic Therapy and Medical Laser Applications, Milan, Jun. 24–27, 1992, P. Spinelli, M. Dal Fante, R. Marchesini, Istituto Nazionale per lo Studio e la Cura dei Tumori, 20133 Milan, Italy, Excerpta Medica, Amsterdam–London–New York–Tokyo, pp. 169–173.

Maxwell et al., 1988, "Insulin–$^{125}$I–Tyramine, an Improved Residualizing Label for Studies on Sites of Catabolism of Circulating Proteins," *Journal of Biological Chemistry* 263(28):14122–14127.

Winkelman, James W., 1967, "Metabolic Studies on the Accumulation of Tetraphenylporphinesulfonate in Tumors," *Experientia* 23(11):949–50.

*Primary Examiner*—William R. A. Jarvis
*Attorney, Agent, or Firm*—Pennie & Edmonds LLP

[57] ABSTRACT

The present invention relates pharmaceutical compositions comprising a conjugate of an active substance, a linker and a carrier for the treatment and/or diagnosis of inflammatory diseases. The present invention further relates to methods using such pharmaceutical compositions for treating and diagnosing inflammatory diseases including, but not limited to, infectious diseases, autoimmune diseases, skin diseases, and inflammatory neovascularization.

10 Claims, 4 Drawing Sheets

CONJUGATE FOR TREATING INFLAMMATORY DISEASES

This is a national phase filing of the Application No. PCT/DE95/01337, filed Sep. 26, 1995, and is entitled to priority of the German Patent Application P 44 35 087.2, filed Sep. 30, 1994.

I. FIELD OF THE INVENTION

The present invention relates to the use of conjugates comprising an active substance, a linker and a carrier, for treating and/or diagnosing inflammatory diseases.

II. BACKGROUND OF THE INVENTION

For treating inflammatory diseases such as infectious and/or autoimmune and/or skin diseases, pharmaceutical preparations which have to be administered in very high doses have been used so far. This represents a major load for the liver. In addition, these pharmaceutical preparations concentrate in many tissues which represents a further load for the body.

DE-A 39 12 792 and DE-A-40 17 439 disclose conjugates of the above kind which can be used for treating and/or diagnosing tumors.

Surprisingly, it has not been found that these conjugates are also suitable for treating and/or diagnosing inflammatory diseases such as infectious and/or autoimmune and/or skin diseases and/or inflammatory neovascularizations, e.g., in the cornea of the eye, without being accompanied by the drawbacks of the pharmaceutical preparations used for this purpose so far.

Thus, the above conjugates are used according to the invention for the treating and/or diagnosing inflammatory diseases such as infectious and/or autoimmune and/or skin diseases, such as psoriasis, and/or inflammatory neovascularizations, e.g., in the cornea of the eye.

III. SUMMARY OF THE INVENTION

The present invention relates pharmaceutical compositions comprising a conjugate of an active substance, a linker and a carrier for the treatment and/or diagnosis of inflammatory diseases. The present invention further relates to methods using such pharmaceutical compositions for treating and diagnosing of inflammatory diseases including, but not limited to, infectious diseases, autoimmune diseases, skin diseases, and inflammatory neovascularization.

IV. BRIEF DESCRIPTION OF THE DRAWINGS

Figure 2:
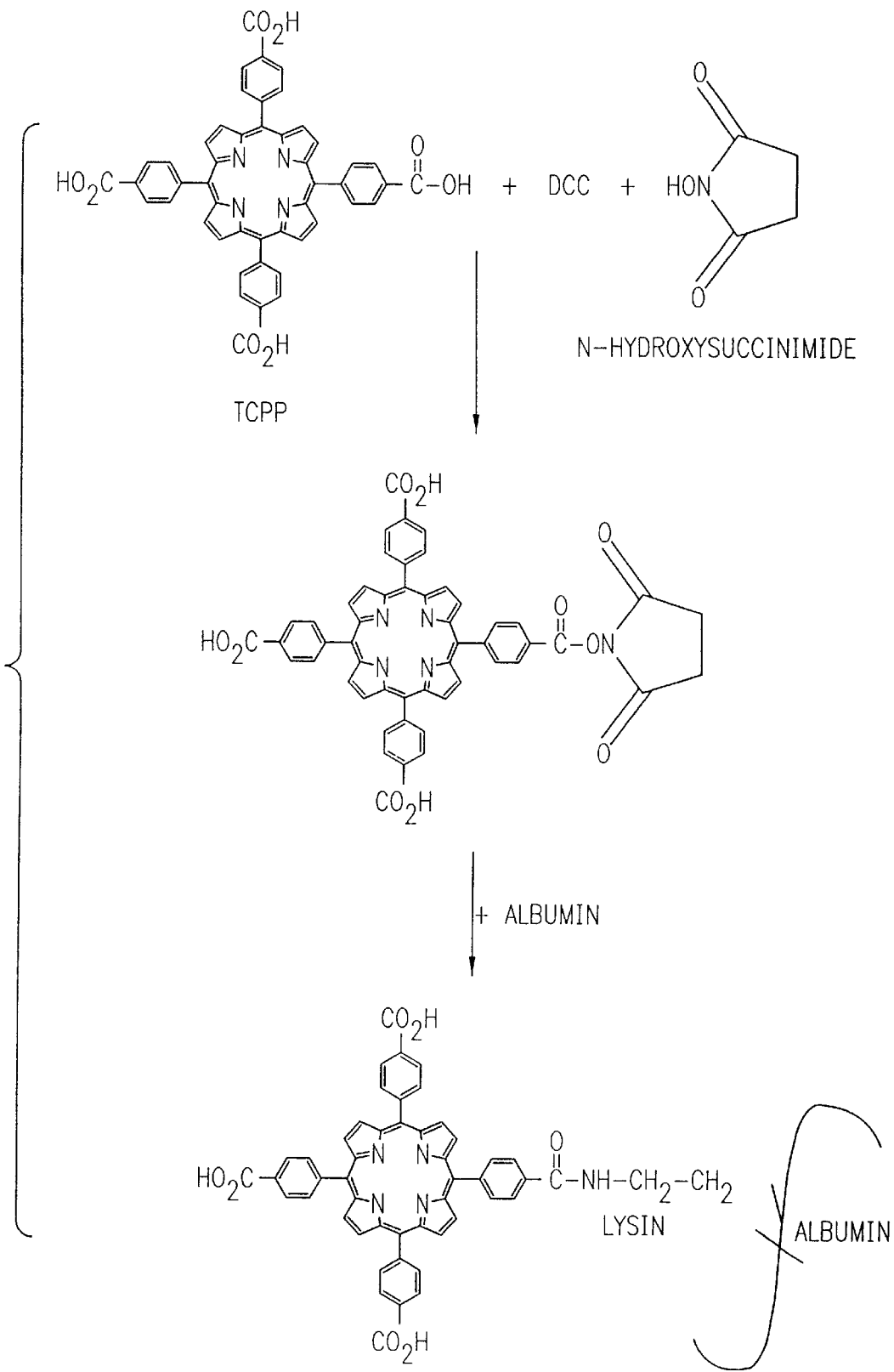
Figure 3:
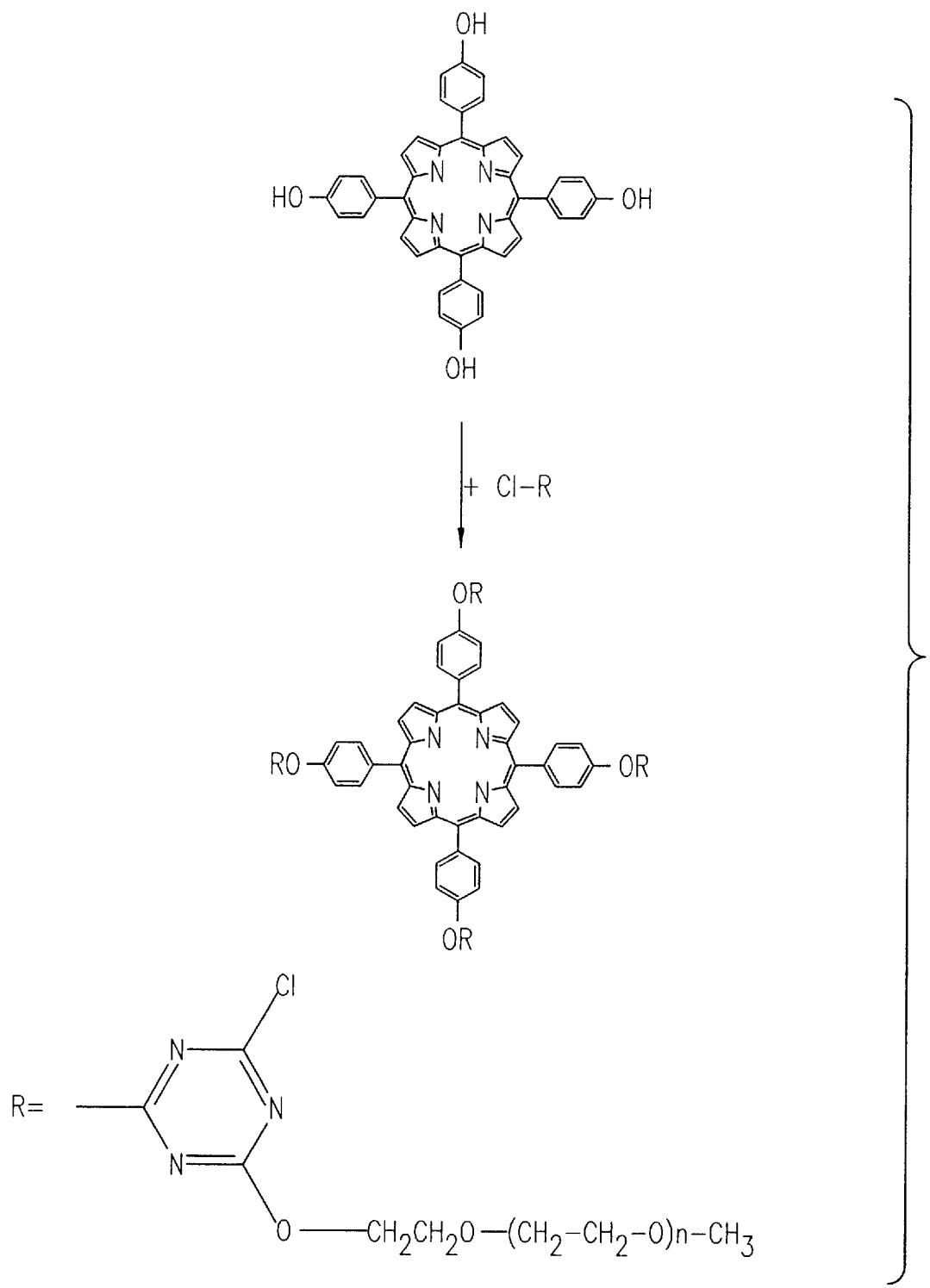
Figure 4:
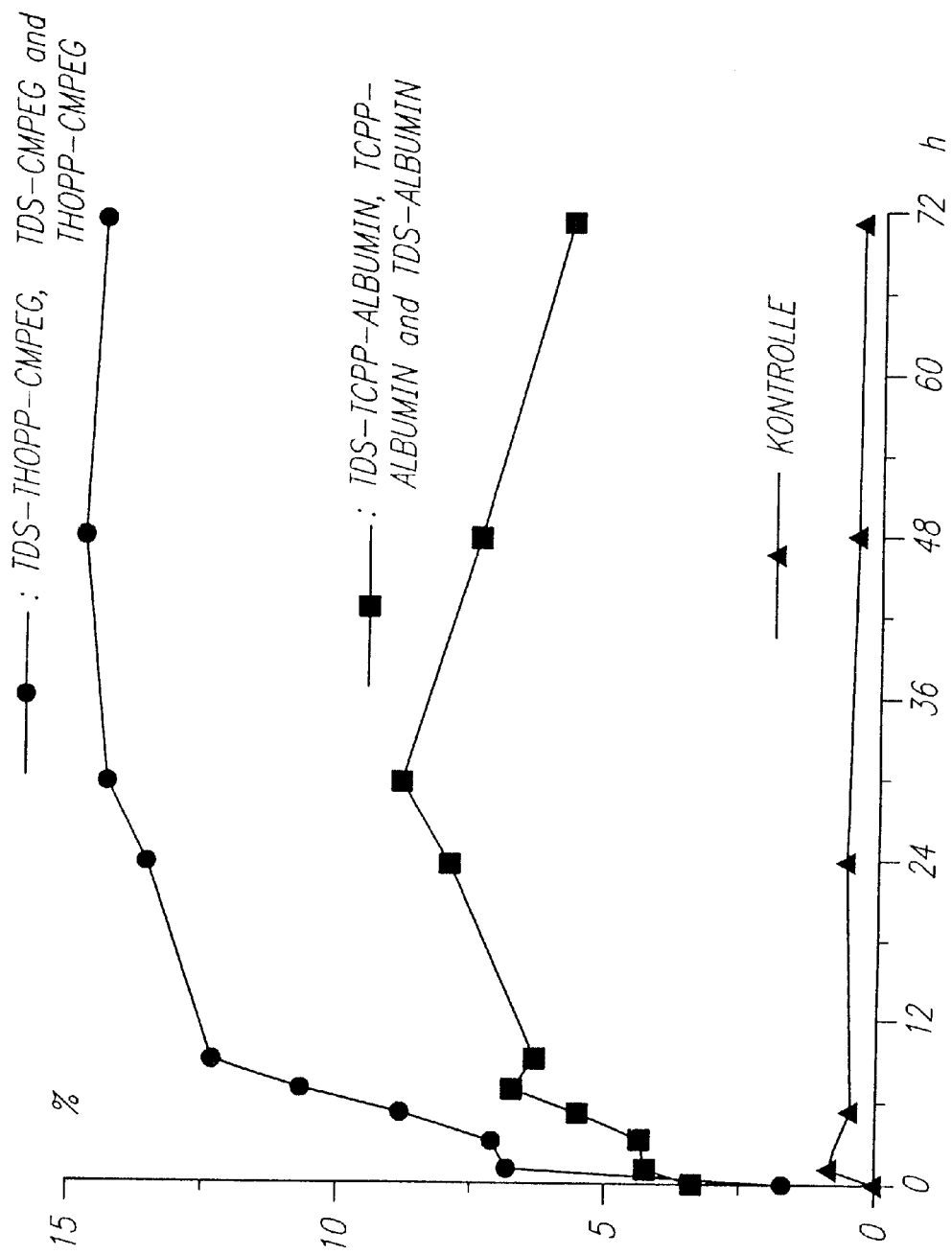

FIG. 1 shows the linkage of radioactively labeled tyramine-N-1'-deoxysorbitol (TDS) to albumin via cyanuric chloride, FIG. 2 shows the linkage of tetracarboxyphenylporphyrin (TCPP) to albumin, FIG. 3 shows the linkage of tetrahydroxyphenylporphyrin (THOPP) to methoxypolyethylene glycol (MPEG) via cyanuric chloride, and FIG. 4 shows the concentration of conjugates in inflammatory tissue.

V. DETAILED DESCRIPTION OF THE INVENTION

The expression "active substance" comprises compounds of any kind which can be used for treating and/or diagnosing inflammatory diseases, particularly infectious and/or autoimmune and/or skin diseases and/or inflammatory neovascularizations. Examples of the above compounds are radioactively labeled aromatic compounds, photodynamically active compounds and chemotherapeutic agents. Examples of photodynamically active compounds are porphyrin derivatives such as tetracarboxyphenylporphyrin (TCPP) and tetrahydroxyphenylporphyrin (THOPP), chlorines and bacteriochlorines. Examples of chemotherapeutic agents are cytostatic agents and antibiotics. Representatives thereof are, e.g., doxorubicin, daunorubicin, tetracycline and derivatives thereof as well as antimetabolites such as methotrexate. The above photodynamically active compounds and chemotherapeutic agents may also be labeled, e.g., by means of a radioactive substance such as iodine. In addition, a conjugate used according to the invention may not only contain a single but also several of the compounds.

The expression "linker" comprises compounds of any kind which are suitable for linking two components of the conjugate, particularly protein and active substance. Examples of such linkers are cyanuric chloride and derivatives thereof which are used as educt for forming the conjugate. Furthermore, a linker may already be part of the active substance, so that no further linker has to be incorporated into the conjugate. An example of this is given in FIG. 2.

The expression "carrier" comprises compounds of any kind which are suitable for concentrating the conjugate in a tissue damaged by an above disease. Examples thereof are proteins which are not considered exogenous and polyethylene glycols (PEG). The former are proteins having a molecular weight of up to 100,000 daltons, particularly 30,000 to 100,000 daltons. Preferably it is albumin, more preferably in native form, and transferrin. Protein fragments may also be used. Examples of polyethylene glycols are those having a polymerization degree n if 5 to 250. The polyethylene glycols are preferably esterified or etherified at the terminal hydroxyl group with a $C_1C_{12}$ alkyl group, particularly methyl group. A PEG etherified by a methyl group is referred to as methoxypolyethylene glycol (MPEG).

A conjugate used according to the invention may also contain a polyalcohol. The latter may preferably be bound to the active substance. The expression "polyalcohol" comprises atomic groups of any kind which have at least one OH group and are not considered exogenous. The compounds used as active substance may also bear a polyalcohol in the molecule. Then, no further polyalcohol has to be incorporated into the conjugate.

Examples of the polyalcohol have the following structure:

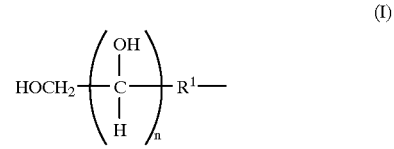

(I)

in which $R^1$ is CHOH, $CH_2$, C=O or $CH_2NH$ and n is at least 1, preferably 1 to 10, and most preferably 3 to 6. An example of such a polyalcohol is a glucamine residue or a derivative thereof.

In addition, the polyalcohol may be a tris(hydroxymethyl)aminoethane residue or a derivative thereof.

Preferably used conjugates are indicated in FIGS. 1 to 3 and in Example 1.

As far as the further disclosure of the conjugates used according to the invention is concerned, reference is made expressly to the above-mentioned DE-A 39 12 792 and DE-A 40 17 439.

Moreover, conjugates used according to the invention can be produced according to conventional methods by which the active substance, the linker, the protein and optionally the polyalcohol are linked with one another. Reference is made in this connection to the production of the conjugates of FIGS. 1 to 3 by way of example.

Conjugates used according to the invention distinguish themselves by an increased half life in the organism, which is partially effected by the little excretion. In addition, the conjugates concentrate in tissue damaged by inflammatory diseases such as infectious and/or autoimmune and/or skin diseases and/or inflammatory neovascularizations. Thus, they are suited in the best possible way for reacting and/or diagnosing inflammatory diseases such as infectious and/or autoimmune and/or skin diseases and/or inflammatory neovascularizations.

The below example explains the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Concentration of Conjugates in Inflammatory Tissue

An inflammation was triggered in the left hind leg of rats by injection of 2 ml of sephadex spheres (Sephadex G-200 Sigma Chemicals). Thereafter, one of the below conjugates each was given to one rat. The conjugates used were:

| | |
|---|---|
| TDS-CMPEG | (CMPEG: cyanuric chloride-activated MPEG (n = 110)), |
| THOPP-CMPEG | (See, FIG. 3), |
| TDS-THOPP-CMPEG | (conjugated in which both CMPEG (n = 110) and TDS are linked to THOPP), |
| TDS albumin | (See, FIG. 1), |
| TCPP albumin | (See, FIG. 2) or |
| TDS-TCPP albumin | (conjugated in which both TDS via cyanuric chloride and TCPP are linked to albumin). |

In place of the sephadex spheres, 2 ml of physiologic salt solution were introduced by injection into rats as control and thereafter one of the above conjugates was applied.

The concentration of the conjugates was documented by means of scintiscanning as usual for 72 hours.

As follows from FIG. 4, the conjugates concentrate in inflammatory tissue as compared to the control.

All references cited within the body of the instant specification are hereby incorporated by reference in their entirety.

We claim:

1. A method for treating an inflammatory disease, comprising administering a pharmaceutical composition comprising a conjugate of an active substance, a linker, and a carrier, wherein said carrier is selected from the group consisting of albumin, transferrin and polyethylene glycol, and the active substance is selected from the group consisting of a radioactively labeled aromatic compound, a photodynamically active compound, and a chemotherapeutic agent.

2. The method of claim 1, wherein the polyethylene glycol is methoxypolyethylene glycol.

3. The method of claim 1, wherein the conjugate has a polyalcohol.

4. The method of claim 3, wherein the polyalcohol has the following structure:

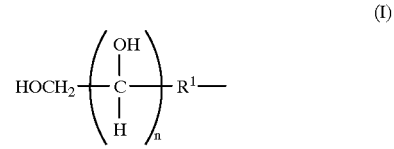

(I)

wherein $R^1$ is selected from the group consisting of CHOH, $CH_2$, C=O and $CH_2NH$; and n is at least 1.

5. The method of claim 1, 2, 3 or 4, wherein the inflammatory disease is selected from the group consisting of an infectious disease autoimmune disease, skin disease, and inflammatory neovascularization.

6. A method for diagnosing an inflammatory disease, comprising:

(a) administering a composition comprising a conjugate of an active substance, a linker, and a carrier to a subject to be diagnosed, wherein said carrier is selected from the group consisting of albumin, transferrin and polyethylene glycol, and the active substance is selected from the group consisting of a radioactively labeled aromatic compound, a photodynamically active compound, and a chemotherapeutic agent; and (b) determining the concentration of radioactive label in different tissues in said subject compared to a control to identify an inflammatory disease.

7. The method of claim 6, wherein the polyethylene glycol is methoxypolyethylene glycol.

8. The method of claim 6, wherein the conjugate has a polyalcohol.

9. The method of claim 6, wherein the polyalcohol has the following structure:

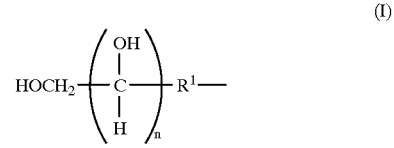

(I)

wherein $R^1$ is selected from the group consisting of CHOH, $CH_2$, C=O and $CH_2NH$; and n is at least 1.

10. The method of claim 6, 7, 8, or 9, wherein the inflammatory disease is selected from the group consisting of an infectious disease, autoimmune disease, skin disease, and inflammatory neovascularization.

* * * * *